United States Patent [19]

Yoshitake et al.

[11] 3,952,037

[45] Apr. 20, 1976

[54] ALUMINUM CATALYSTS

[75] Inventors: Hiroshi Yoshitake, Oita; Kenji Tanimoto, Minoo; Norio Kotera, Amagasaki, all of Japan

[73] Assignee: Sumitomo Chemical Company, Limited, Osaka, Japan

[22] Filed: May 24, 1973

[21] Appl. No.: 363,699

[30] Foreign Application Priority Data
May 26, 1972 Japan.............................. 47-052759

[52] U.S. Cl................................ 260/448 R; 23/283; 252/431 R; 260/448 A; 260/668 A; 260/668 B; 260/671 C
[51] Int. Cl.² ............................................ C07F 5/06
[58] Field of Search ........ 260/448 R, 668 A, 668 B, 260/671 C

[56] References Cited
UNITED STATES PATENTS

| 3,000,919 | 9/1961 | Wetroff et al.................... | 260/448 R |
|---|---|---|---|
| 3,148,226 | 9/1964 | Schneider et al. ............... | 260/674 R |
| 3,374,257 | 3/1968 | Walker............................ | 260/448 R |
| 3,398,206 | 8/1968 | Strohmeyer et al. ........... | 260/668 A |
| 3,565,965 | 2/1971 | Walker et al.................... | 260/674 SE |
| 3,755,155 | 8/1973 | Cier............................ | 260/674 SE X |
| 3,766,290 | 10/1973 | Carlson........................ | 260/671 C X |

FOREIGN PATENTS OR APPLICATIONS
1,180,617    2/1970   United Kingdom

OTHER PUBLICATIONS

Thomas, Anhydrous Aluminum Chloride in Organic Chemistry, Reinhold Publ. Corp., N.Y., pp. 846–847, (1941).
Chem. Abstracts, Vol. 51, 12843g, (1957).
Chem. Abstracts, Vol. 55, 16453f, (1961).
Chem. Abstracts, Vol. 65, 1460d, (1966).

*Primary Examiner*—Helen M. S. Sneed
*Attorney, Agent, or Firm*—Sughrue, Rothwell, Mion, Zinn & Macpeak

[57] ABSTRACT

An aluminum halide complex of an aluminum halide, a hydrogen halide and an alkylbenzene is prepared by continuously feeding a gaseous hydrogen halide to a reaction zone comprising aluminum and an alkylbenzene and continuously taking the resulting aluminum halide complex out of the reaction zone, the byproduced hydrogen gas being taken out of the reaction zone, and aluminum and the alkylbenzene being fed continuously or intermittently to the reaction zone.

15 Claims, 2 Drawing Figures

ALUMINUM CATALYSTS

The present invention relates to a method for producing liquid aluminum catalysts which are complexes between aluminum halides, alkylbenzenes and hydrogen halides, the catalysts being referred to as an aluminum halide complex hereinafter, and to an apparatus for the preparation thereof.

Anhydrous aluminum halides, especially anhydrous aluminum chloride, are essential as catalysts for the so-called Friedel-Crafts Reaction and the analogous reactions thereof which include alkylation, trans-alkylation, isomerization, acylation and the like.

These catalysts of anhydrous aluminum halide series are usually employed in the lump or granular form, or in the finely pulverized form.

Anhydrous aluminum halides have however some serious difficulties when applied for a large scale production, especially for a continuous production. The reason is that these catalysts are very difficult, in a practical use, to be handled in a large amount and to be supplied continuously and quantitatively in a solid form to a reaction system. In order to avoid these difficulties, anhydrous aluminum halide is supplied in a powder form, however it sometimes solidifies at a feed nozzle of a reactor, or on the way to the nozzle to plug the nozzle, or liberates irritating or corrosive gases, thereby interrupting a normal operation of the plant and sometimes losing remarkably its catalytic activity, if it is treated improperly. Furthermore, the pulverization of anhydrous aluminum halide requires a very troublesome and difficult process for the same reason as mentioned above, thereby remarkably increasing the cost of pulverized anhydrous aluminum halide.

In order to avoid these difficulties, an attempt has been made to produce a catalytically active matter by reacting aluminum powder supplied to an alkylating reaction system with hydrogen halide which is supplied to the system or produced in the system, however it has disadvantages that the pulverization of aluminum becomes high-priced, the difficulties accompanied by the supply in a solid form still remain unsolved and that the aftertreatment of unreacted aluminum is troublesome. In addition to the above, the inevitable time lag from the supply of aluminum to the formation of catalytically active matters makes it difficult to control the reaction, and the resulting hydrogen increases by-products by the reductive action thereof.

It has also been reported that aluminum chloride complexes are formed by introducing dried hydrogen chloride gas for 2.5 to 3 hours in a suspension of a small amount of aluminum-copper alloy particles in ethylbenzene, the aluminum alloy being used in order to protect the benzene nucleus of ethylbenzene from hydrogenation. Complexes obtained by this method contain copper chloride as an insoluble matter and in addition they are much different from those obtained from aluminum alone in the activity to the Friedel-Crafts Reaction and the like, and therefore they are limited in the use thereof. Furthermore the previous preparation of alloys having a required composition for this purpose and the pulverization thereof are very disadvantageous from economical point of view.

Another method is proposed to prepare a liquid aluminum chloride catalyst by passing a vapour of alkylbenzenes through anhydrous aluminum chloride bed. This process ensures the smooth supply of catalyst to a reaction system, however it also encounters many difficulties in a practical operation. The reason is that anhydrous aluminum chloride to be packed should be uniform, in particle sizes thereof, otherwise it does not permit the operation to proceed smoothly, and that the packed aluminum chloride disappears or collapses by the rapid dissolution thereof, whereby the particle sizes and the state of bed change all the time thereby causing a danger of the collapse and plugging of the bed. Furthermore in the case of a continuous process, how to supply continuously granular anhydrous aluminum chloride still remains unsolved, and on the other hand in the case of a batch process, a troublesome supplement of the packing is required. Still further a liquid aluminum chloride catalyst thus obtained has disadvantageously a little lower activity than anhydrous aluminum chloride does.

The inventors have made extensive studies to overcome the above mentioned defects, that is, the difficulty in the handling of solid aluminum halide, the deterioration in activity of the catalyst, the high preparation cost, the formation of nuclear-hydrogenated hydrocarbons due to the use of powdered or finely pulverized aluminum, and the various difficulties accompanied by the above, and have accomplished this invention.

The present invention is to provide a method for producing an aluminum halide complex of an aluminum halide, a hydrogen halide and an alkylbenzene, which comprises continuously feeding a hydrogen halide to a lower part of a reaction zone comprising aluminum and an alkylbenzene, and continuously taking the resulting aluminum halide complex out of a lower part of the reaction zone, the by-produced hydrogen gas being taken out of an upper part of the reaction zone, the aluminum and the alkylbenzene each being continuously or intermittently fed to the reaction zone.

Aluminum to be used in the present invention need not be of specially high purity and can sufficiently be used in a technical grade. Aluminum alloys containing a large amount of other metals such as copper produce insoluble matters, thereby sometimes interrupting a continuous operation or giving undesirable effect on the activity of catalyst. Aluminum placed in the reaction zone is a small piece, and can be used in any shape and dimension, provided that it gives suitable ratios of space and surface area when packed in a catalyst-producing apparatus. For example those which are shaped like packing generally used in a packed tower, e.g., a saddle, spiral, wire net or ring type, may be preferred, and lathe chips, a pellet-, ball-, rod- or granule-type may also satisfactorily be used practically. Relating to the dimension, packing of any dimension can sufficiently be used, provided that a ratio of diameters of the tower to packing is within a range used for common packed towers and furthermore even those having a wider range can also be used. In a practical use, those of about 3 to 100 mm in an average diameter can conveniently be used.

These pieces of aluminum are fed from a top of the apparatus to a reaction zone continuously or intermittently. The use of aluminum as a material has advantages that it not only reduces the cost, but also increases the strength and stability of packed bed, and makes easy the handling and storage of aluminum. Moreover, the amount of aluminum pieces to be supplemented is very small compared with that of catalyst to be produced, for example the amount of aluminum to be supplemented is only about one-fifth by weight ratio based on anhydrous aluminum chloride to be produced and is really only about one-tenth based on anhydrous aluminum bromide to be produced, and the time intervals between individual intermittent supplements of aluminum pieces can be much extended, thereby a substantially continuous operation being made possible. And furthermore the processing cost of aluminum pieces is extremely low compared with the manufacturing cost of powdered anhydrous aluminum chloride or finely powdered aluminum. The bed of aluminum pieces in the reaction zone is dipped in alkylbenzenes.

The alkylbenzenes have at least one primary or secondary alkyl group having up to 6 carbon atoms and preferably they are either a starting material for or a product in the Friedel-Crafts Reaction. It is desirable that those having a fused ring, such as naphthalene, anthracene or phenanthrene, are not used, because the ring is relatively unstable to aluminum halides or the complexes thereof. Benzenes having no alkyl groups can not be used for the preparation of the complexes as they are incapable of forming aluminum halide complexes, except that they are used as a diluent for other alkylbenzenes. Especially suitable alkylbenzenes include toluene, ethylbenzene, diethylbenzenes, triethylbenzenes, ethyltoluenes, diethyltoluenes, xylenes, trimethylbenzenes, tetramethylbenzenes, ethylxylenes, isopropylbenzene, diisopropylbenzenes, triisopropylbenzenes, isopropyltoluenes, diispropyltoluenes, isopropylxylenes, isopropylethylbenzenes, sec.-butylbenzene, di-sec.-butylbenzenes, sec.-butyltoluenes, di-sec.-butyltoluenes, sec.-butylxylenes, sec.-butylethylbenzenes, hexylbenzene, cyclohexylbenzene and the mixtures thereof. Benzene may be used in admixture with the alkylbenzene although it is not a material for complexes.

Hydrogen halides can sufficiently be used if it is dried to a general extent, for example, as low as 0.1% of water. They may contain free hydrogen and halogens therein to a certain extent, and for an industrial purpose hydrogen chloride and hydrogen bromide are favorable. The feed velocity of the hydrogen halide to the reaction zone is preferably 1 to 500 mm/sec. in a superficial velocity in a usual column. In another aspect, the molar ratio to aluminum of the hydrogen halide to be fed is appropriately selected from a range between 1/100 and 10 mol/hour. the reaction temperatures vary according to the type of alkylbenzenes and hydrogen halides and the ratio of surface area of aluminum bed, however, a range of about 40° to 200°C is preferable. Too much low temperatures reduce a reaction velocity and too much high ones easily cause the formation of by-products, the deterioration of catalytic activity of resulting complexes and the tarification, resulting in economical disadvantages in any case. This reaction is considerably highly exothermic, however the heat of reaction liberated can be removed from the reaction system by the evaporation of alkylbenzenes and/or by cooling the reaction zone. In the former case a reaction temperature may be controlled by adding an inert substance having a suitable boiling point to alkylbenzenes. The resulting complexes are separated from the alkylbenzene layer and immediately fall down due to the difference between specific gravities of both. On the other hand the resulting hydrogen gas also immediately escapes upwards out of the system, and so the hydrogenation of alkylbenzenes due to the extended contact of the complexes with hydrogen can be remarkably avoided.

The aluminum halide complexes thus prepared have the same or more highly catalytic activity to the Friedel-Crafts Reaction and the analogous reactions thereof as that of the same molar anhydrous aluminum halide as contained in the complexes. The present invention is also to provide an apparatus for the preparation of an aluminum halide complex of an aluminum halide, a hydrogen halide and an alkylbenzene, characterized by comprising a reactor in which aluminum and the alkylbenzene are placed, the reactor having an inlet at an upper part through with aluminum is continuously or intermittently fed, another inlet at a lower part through which the hydrogen halide is continuously fed, another inlet through which the alkylbenzene is continuously or intermittently fed, and an outlet at an upper part through which the by-produced hydrogen gas is taken off, and the reactor being connected to an upper part of a holder in which the resulting aluminum halide complex is collected.

FIG. 1 and FIG. 2 concretely illustrate an embodiment of the present apparatus.

The present invention will be illustrated in more detail with reference to the accompanying drawings.

Figure 2:
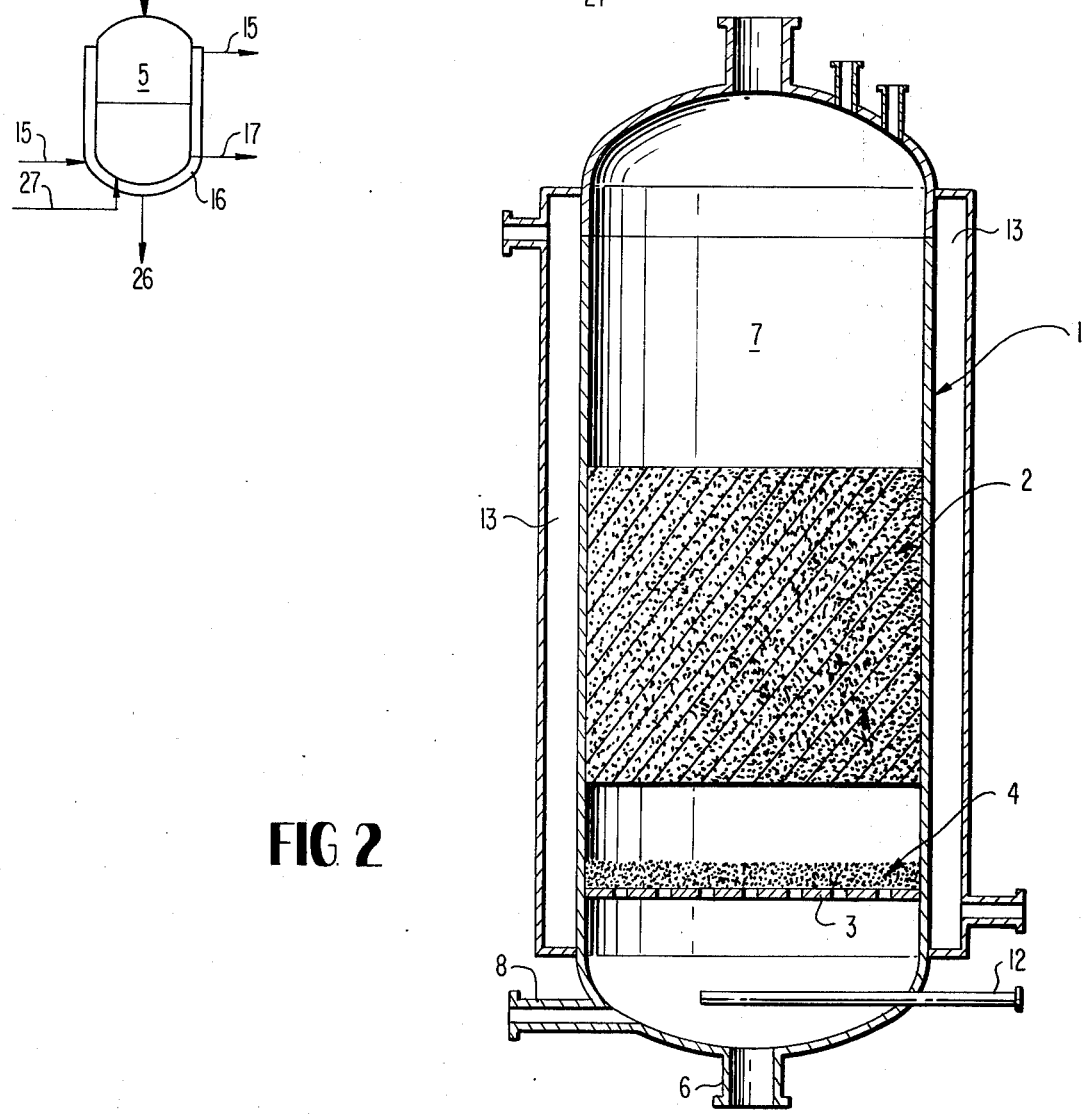
FIG. 2 illustrates the details of the construction of a catalyst-producing reactor 1.

A catalyst-producing reactor 1 is made of an anticorrosive material and is packed with aluminum pieces as shown in FIG. 2. An aluminum-packed bed 2 is supported by a perforated-plate 3 and, if desired, a bed 4 packed with a small amount of an anti-corrosive material on the plate. under the reactor 1 is placed a settling and storage holder 5, and both are connected to each other by a thick pipe 6. Alkylbenzenes are filled in the holder 5 and the reactor 1 to the level over the upper end of the aluminum packed bed 2. Alkylbenzenes are supplemented through a pipe 8 so as to maintain the level of the liquid surface within a definite range. Aluminum pieces are intermittently fed to the reactor 1 through a thick pipe 10 from a hopper 9. The atmosphere in the reactor 1, and in the all systems connecting with the upper part of the reactor including the hopper is replaced by an inert gas such as nitrogen fed through a pipe 11. Hydrogen halides are fed through a pipe 12, the end of which is made so as to distribute the halides efficiently. The reactor 1 is fitted with a jacket 13 through which a cooling or heating medium is passed from a pipe 14 to cool or heat the reactor. The beginning of reaction needs heating, however cooling is required while the reaction is proceeding constantly.

Liquid aluminum halide complexes formed by the reaction immediately fall down through gaps within the packed bed into the settling and storage holder 5, wherein the complexes are collected. The settling and storage holder 5 is cooled to a definite temperature by a cooling medium which is passed through a jacket 16 attached to the holder from a pipe 15. Aluminum halide complexes thus obtained are continuously taken out of the holder 5 through a pipe 17 fitted to the holder at the level a little higher above the bottom thereof. An amount of the complexes to be taken out is controlled to maintain level of the liquid surface thereof within a definite range.

Hydrogen generated during the reaction, unreacted hydrogen halide gas and vapour of the alkylbenzene are passed through a pipe 18 to a condenser 19 where the vapour of alkylbenzene is condensed and returned back to the reactor 1 via a pipe 20. Non-condensing gases are passed through a pipe 21 to an absorber 22 where the gases contact with an absorbing-liquid fed through a pipe 23, thereby hydrogen halide gas transferred into a liquid phase by absorption being discharged through a pipe 24 and residual gases consisting mainly of hydrogen gas being discharged through a pipe 25.

Aluminum pieces within the packed bed 2 become smaller in size with the progress of the reaction, however as this phenomenon occurs all over the bed, it is hardly observed that the collapse of packed bed and the deflection of streams occur by a partial solving out of the bed. An amount of small aluminum pieces which fall down to the settling-holder 5 through gaps within the packed bed 4 is too small to cause a problem in a practical operation. A pipe 26 fitted to the bottom of the holder 5 is intended to intermittently discharge insoluble matters due to an extremely small amount of impurities contained in aluminum as a material, or unreacted small pieces of aluminum which may possibly be present. The settling-holder 5 may be fitted with a pipe 27 so as to feed a sealing inert gas and, if necessary, an additional hydrogen halide.

When a boiling point of a reaction solution is higher than a reaction temperature, the removal of the heat of reaction by an evaporation of the solution can not be expected. In this case the heat of reaction can be removed in combination with a method by which an alkylbenzene layer in a reaction system is cooled by the circulation thereof through a heat exchanger, which is however not illustrated in the Figure.

According to the apparatus above mentioned, the resulting complexes quickly fall down out of the reaction system and cooled, on the other hand hydrogen gas quickly escapes into an gaseous phase above the system whereby the hydrogenation of alkylbenzene is substantially negligible and the elimination and rearrangement of alkyl groups are not so serious except a tertiary group.

According to the present invention as illustrated hereinbefore, highly active catalyst complexes which are useful for the Friedel-Crafts Reaction such as alkylation, acylation, isomerization, trans-alkylation and the like can safely, cheaply and continuously be produced even in a large scale production. The present invention will furthermore concretely be illustrated with reference to the following examples.

EXAMPLE 1

A glass reaction column of 70 mm in diameter was packed with 540 g of lathe chips of aluminum which were cut into 15 to 25 mm in length to make a packed bed and 2000 g of toluene were further added thereto. Dried hydrogen chloride gas was blown into the bed at the bottom thereof at a rate of about 250 g per hour. The reaction system reached its boiling point 1 hour after the starting of reaction and the reaction was continued at 150° to 107°C under reflux. The resulting aluminum chloride complex was taken out from the bottom and stored in a storage-holder. Toluene was supplemented as the amount of toluene decreased. After 4 hours' reaction, 193 g of aluminum were consumed and 3670 g of a brown aluminum chloride complex were obtained. The complex contained 26% of aluminum chloride and 3% of hydrogen chloride, and the rest was organic components. This complex was stored in a closed vessel for the following test.

EXAMPLE 2

A glass reaction column of 40 mm and 700 mm in diameter and length respectively which is capable of heating and cooling by jacket was packed with aluminum pellets of 10 mm and 3 mm in diameter and thickness respectively up to a level of 500 mm from the bottom and then was filled with a mixture of 10 % by weight of benzene and 90% by weight of sec.-butylbenzene. After heating the column up to 90°C, dried hydrogen chloride gas was passed therethrough at a rate of 22.4 Nl per hour and then immediately the column was cooled by passing a cooling water through a jacket to such an extent that a reflux in a condenser might slightly be observed. As a result of the reaction at 90°C for 4 hours, an average velocity at which a complex has been formed was 113 g per hour and an average velocity at which aluminum had been consumed was 7.25 g per hour, and the presence of hydrogen chloride could not be observed in a waste gas. It was found that this complex was effective as a catalyst for the preparation of mono- and disec. -butylbenzene from benzene and n-butene.

EXAMPLE 3

Figure 1:
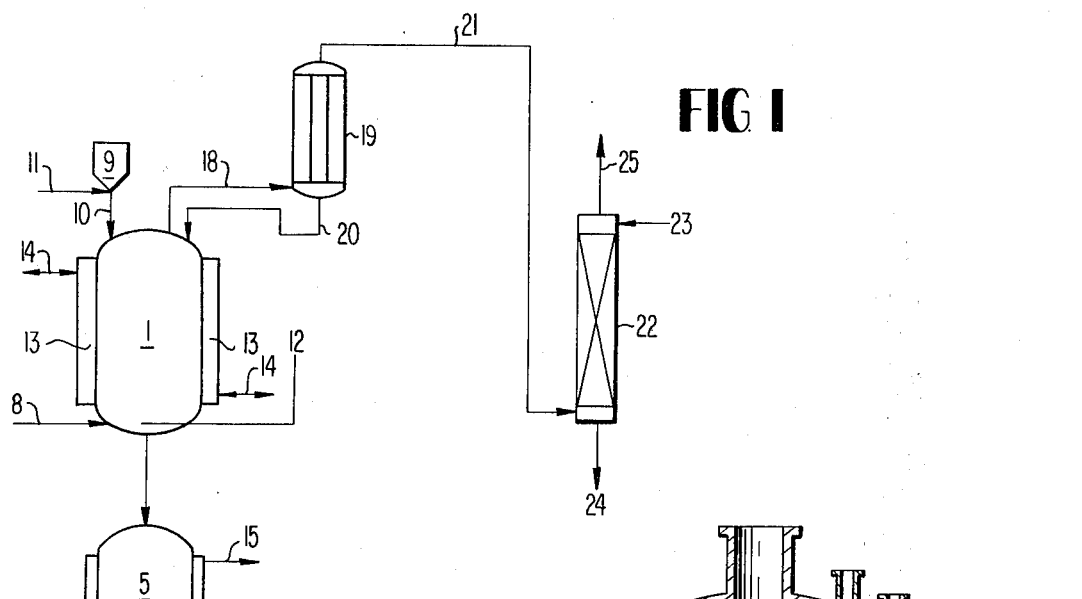
FIG. 1 shows only illustrative apparatus for the preparation of catalysts.

In an apparatus in FIG. 1 a packed bed 4 was replaced by a combined bed consisting of one bed having Raschig rings of 7 mm in diameter made of porcelain packed to a level of 20 cm from a perforated-plate, and another bed having aluminum falls of about 2.5 cm in diameter made of 99.7% purity grade packed in height of 67 cm above the former bed. Toluene was fed to a level of 100 cm above the plate, air was removed from the column by the streams of nitrogen gas from a pipe 9 and then hydrogen chloride gas was introduced at a rate of 2.4 cm per second (a linear velocity in empty tower of the gas in the standard state) at a ring-shaped and perforated end of a pipe 12. Toluene was refluxed at 110° to 113°C. The resulting aluminum chloride complex fell down into a settling-holder 5 maintained at 50°C and was collected under the toluene layer. When the aluminum chloride complex in the settling-holder was taken out of the holder through a pipe 17 so as to hold the upper surface at a definite level, it was found that a falling velocity of the surface of toluene layer corresponded to about 38 cm per hour, therefore the corresponding amount of toluene was supplemented through a pipe 8 to hold the level of a toluene layer 7 constant. After a 24 hours' reaction, the level of an aluminum bed was decreased to 23 cm, and so the blowing of hydrogen chloride was stopped and aluminum balls were supplemented in such an amount that an initial height of 67 cm might be restored, from a hopper 9 which was previously charged with a required amount of aluminum balls and replaced by an atmosphere of nitrogen gas, and immediately the blowing of hydrogen chloride was started again. The surface of toluene was raised temporarily and then descended to an initial level by the consumption thereof, thereafter was supplemented as mentioned above. Gases which were not condensed in a condenser 19 were hydrogen chloride and hydrogen, and the hydrogen chloride was absorbed in a dilute hydrochloric acid in an absorber 22 packed with Raschig rings of porcelain, and recovered through a pipe 24 as hydrochloric acid. An amount of hydrogen chloride recovered was confirmed to be about 9% by weight of hydrogen chloride fed to a reactor 1 on the base of the material balance for 24 hours. Hydrogen gas discharged from a pipe 25 was washed with an alkali solution and used as a fuel.

The aluminum chloride complex thus obtained was about 19 times by weight based on an amount of consumed aluminum and was used continuously in the preparation of isopropyltoluene from toluene and propylene and in the preparation of isopropyltoluene from toluene and diisopropyltoluene.

EXAMPLE 4

In Example 1, hydrogen chloride was replaced by hydrogen bromide of 555 g per hour. To 656 g of oily complex thus obtained (267 g as aluminum bromide) were added 80 g of acetylchloride at 25° to 30°C and then the mixture was held at 70°C for 1 hour. Thereafter the solution was treated with a dilute hydrochloric acid, water and a caustic soda solution in this order. Toluene was removed by rectification to give 125 g of o- and p-methylacetophenone.

EXAMPLE 5

Example 1 was repeated except that a mixture of 5% of benzene and 95% of cumene was used in place of toluene, hydrogen chloride gas was bubbled at 85°C, and the reaction was continued for 2 hours, whereby about 1800 g of a complex containing 30% of aluminum chloride (as $AlCl_3$) and 4% of hydrogen chloride was prepared.

A mixture of 43.4 g of benzene and 148 g of triisopropylbenzene was reacted at 100°C for 1 hour in the presence of 2.7 g (0.8 g as $AlCl_3$) of the prepared complex, whereby there was obtained a reaction mixture containing 2.5% of benzene, 25.0% of cumene, 58% of m- and p-diisopropylbenzene and 14% of 1,3,5-triisopropylbenzene.

For the comparison, the reaction was carried out according to the procedure similar to that mentioned above except that 0.8 g of a reagent of anhydrous aluminum chloride was used in place of the aforesaid complex, and then similar results were obtained with an m- an and p-diisopropylbenzene content of 56.5%.

REFERENTIAL EXAMPLE 1

To a mixture of 3.8 g of the complex obtained in Example 1 and 97.3 g of toluene were added dropwise 83 g of ethylbromide at 20° to 25°C over 1 hour and a half while stirring. The reaction solution was held at 50° to 60°C for 1 hour after a dropwise addition, washed with water then alkali and rectified to obtain 64.2 g of ethyltoluene distillate. The resulting distillate was a mixture consisting of m- and p-isomers as main ingredients and a msall amount of o-isomer.

REFERENTIAL EXAMPLE 2

To 3.5 g of the complex obtained in Example 1 were added 60 g of toluene and 60 g of diisopropyltoluene, and the mixture was reacted at 100°C for 4 hours to obtain a reaction mixture containing 28.5% of toluene, 55.0% of isopropyltoluene isomers and 13.5% of diisopropyltoluene isomers. This result was substantially the same as that obtained with the same reaction except that 1 g of aluminum chloride was used in place of the complex mentioned above.

REFERENTIAL EXAMPLE 3

To a mixture of 108 g of the complex obtained in Example 1 and 92 g of toluene were added gradually 14.8 g of phthalic anhydride while stirring, and the mixture was maintained at 70°C for 2 hours after the addition. The reaction mixture was treated as usual to obtain 22.8 g of o-(p-toluyl)-benzoic acid.

REFERENTIAL EXAMPLE 4

In Example 1, a mixture of 50% by weight of benzene and 50% by weight of diethylbenzene was used in place of toluene, and hydrogen chloride gas was passed through at about 90°C for 3 hours and a half to obtain 2460 g of a complex containing 30% of aluminum chloride and 4% of hydrogen chloride. This complex was used in the preparation of ethylbenzene from benzene and ethylene to give a little better result than does powdered anhydrous aluminum chloride used in an equimolar amount.

REFERENTIAL EXAMPLE 5

The complex obtained in Example 1 contained 2.7% of nuclear-hydrogenated compound. When hydrogen chloride gas was passed through a dispersion of 30 g of aluminum powder in 1 l of toluene under reflux for three hours while stirring, it was found that the resulting complex contained 5.6% of a corresponding compound. When the same procedure was carried out with finely powdered aluminum alloy containing 2.1% of copper, the content was about 3 to 3.5% although it was not so correct under the effect of insoluble matters and the like.

The same procedure was carried out as in Example 3 except that an aluminum complex obtained from a copper-containing alloy was used instead, and 37.6% of toluene, 35.9% of cymene and 26.4% of diisopropyltoluene were obtained.

While the invention has been described in detail and with reference to specific embodiments thereof, it will be apparent to one skilled in the art that various changes and modifications can be made therein without departing from the spirit and scope thereof.

What is claimed is:

1. A method for producing an aluminum halide complex of an aluminum halide, a hydrogen halide and an alkylbenzene, which comprises continuously feeding gaseous hydrogen halide to a lower part of a reaction zone containing the aluminum and the alkylbenzene, and continuously removing the resulting aluminum halide complex from a lower part of the reaction zone, by-produced hydrogen gas being removed from an upper part of the reaction zone, wherein each of the aluminum and the alkylbenzene are continuously or intermittently fed to the reaction zone separate from each other in an amount sufficient to supplement the amounts thereof consumed in the formation of said complex.

2. The method according to claim 1, wherein the reaction zone is kept at a temperature of 40° to 200°C.

3. The method according to claim 1, wherein the feed velocity of the hydrogen halide to the reaction zone is 1 to 500 mm/sec. in superficial velocity under standard conditions.

4. The method according to claim 1, wherein the hydrogen halide is hydrogen chloride.

5. The method according to claim 1, wherein the alkylbenzene has at least one primary or secondary alkyl group having up to 6 carbon atoms.

6. The method according to claim 1, wherein the alkylbenzene is at least one member selected from the group consisting of toluene, ethylbenzene, diethylbenzenes, triethylbenzenes, ethyltoluenes, diethyltoluenes, xylenes, trimethylbenzenes, tetramethylbenzenes, ethylxylenes, isopropylbenzene, diisopropylbenzenes, triisopropylbenzenes, isopropyltoluenes, diisopropyltoluenes, isopropylxylenes, isopropylethylbenzenes, sec.-butylbenzene, di-sec.-butylbenzenes, sec.-butyltoluenes, di-sec.-butyltoluenes, sec.-butylxylenes, sec.-butylethylbenzenes, hexylbenzene and cyclohexylbenzene.

7. The method according to claim 1, wherein aluminum in the reaction zone is supported by a perforated plate.

8. The method according to claim 1, wherein said aluminum comprises particles of about 3 to 100 mm., in diameter.

9. The method according to claim 1, wherein said alkyl benzene is present with and is added with a benzene diluent.

10. The method according to claim 1, wherein said hydrogen halide is hydrogen bromide.

11. The method according to claim 1, wherein the reaction solution has a boiling point higher than the reaction temperature and the alkyl benzene layer is cooled by circulation through a heat exchanger.

12. The method according to claim 1, wherein there is further added to said reaction zone benzene as a diluent.

13. The method according to claim 1, wherein said hydrogen halide is fed to said reaction zone at a molar ratio to aluminum of from between 1/100 to 10 mol/hr.

14. The method of claim 1, wherein the temperature is from 40° to 200°C.

15. The method of claim 1, wherein said reaction is conducted under nitrogen.

* * * * *